United States Patent
Rosenblood et al.

(10) Patent No.: US 7,273,369 B2
(45) Date of Patent: Sep. 25, 2007

(54) CURING LIGHT

(75) Inventors: Kenneth Rosenblood, Los Angeles, CA (US); Nancy N. Quan, North Hills, CA (US); Eric P. Rose, Tarzana, CA (US)

(73) Assignee: Discus Dental, LLC, Culver City, CA (US)

(*) Notice: Subject to any disclaimer, the term of this patent is extended or adjusted under 35 U.S.C. 154(b) by 0 days.

(21) Appl. No.: 11/173,264

(22) Filed: Jun. 30, 2005

(65) Prior Publication Data

US 2006/0024638 A1    Feb. 2, 2006

Related U.S. Application Data

(60) Provisional application No. 60/594,327, filed on Mar. 30, 2005, provisional application No. 60/594,297, filed on Mar. 25, 2005, provisional application No. 60/664,696, filed on Mar. 22, 2005, provisional application No. 60/658,517, filed on Mar. 3, 2005, provisional application No. 60/631,267, filed on Nov. 26, 2004, provisional application No. 60/585,224, filed on Jul. 2, 2004.

(51) Int. Cl.
  *A61C 3/00* (2006.01)
  *F21V 20/00* (2006.01)

(52) U.S. Cl. .......... 433/29; 362/800; 362/804

(58) Field of Classification Search .......... 433/29; 362/572, 573, 294, 119, 800, 804; 257/707
See application file for complete search history.

(56) References Cited

U.S. PATENT DOCUMENTS

| | | | |
|---|---|---|---|
| 4,615,679 A | 10/1986 | Wyatt | |
| 4,822,278 A | 4/1989 | Oliva et al. | |
| 5,420,768 A | 5/1995 | Kennedy | |
| 5,634,711 A | 6/1997 | Kennedy | |
| 5,788,499 A | 8/1998 | Hoffman | |
| 5,791,898 A | 8/1998 | Maissami | |
| D413,382 S | 8/1999 | Maissami | |
| 5,954,715 A | 9/1999 | Harrington et al. | |
| 5,971,755 A | 10/1999 | Lieberman et al. | |
| D417,277 S | 11/1999 | Maissami | |
| D419,238 S | 1/2000 | Maissami | |
| D423,100 S | 4/2000 | Maissami | |
| D426,306 S | 6/2000 | Maissami | |
| 6,077,073 A | 6/2000 | Jacob | |
| D427,681 S | 7/2000 | Maissami | |
| 6,159,005 A | 12/2000 | Herold | |
| 6,200,134 B1 | 3/2001 | Kovac | |
| 6,208,788 B1 | 3/2001 | Nosov | |

(Continued)

FOREIGN PATENT DOCUMENTS

WO    WO 99 16136    4/1999

*Primary Examiner*—Cary E. O'Connor
(74) *Attorney, Agent, or Firm*—Nancy N Quan

(57) ABSTRACT

The present invention relates to a curing light suitable for curing light curable dental composite materials. The curing light device has a light module housing having at least one heat sink located therein. The heat sink has at least two mounting platforms arranged in different geometric arrangements. More than two light sources may be used, emitting at least two different wavelengths. The curing light includes at least one heat sink having various geometric shapes, which facilitate the arrangement of the light sources in the curing light and minimizing the concentration.

45 Claims, 12 Drawing Sheets

U.S. PATENT DOCUMENTS

| | | |
|---|---|---|
| 6,274,924 B1 | 8/2001 | Carey |
| 6,318,996 B1 | 11/2001 | Melikechi |
| 6,331,111 B1 | 12/2001 | Cao |
| 6,391,283 B1 | 5/2002 | Jensen et al. |
| 6,419,483 B1 | 7/2002 | Adam et al. |
| 6,439,888 B1 | 8/2002 | Boutoussov et al. |
| D462,444 S | 9/2002 | Maissami |
| 6,468,077 B1 | 10/2002 | Melikechi |
| 6,498,355 B1 | 12/2002 | Harrah |
| 6,514,075 B1 | 2/2003 | Jacobs |
| 6,616,447 B1 | 9/2003 | Rizoiu |
| 6,692,251 B1 | 2/2004 | Logan |
| 6,692,252 B2 | 2/2004 | Scott |
| 6,695,614 B2 | 2/2004 | Plank |
| 6,702,576 B2 | 3/2004 | Fischer |
| 6,709,128 B2 | 3/2004 | Gordon et al. |
| 6,719,558 B2 | 4/2004 | Cao |
| 6,719,559 B2 | 4/2004 | Cao |
| 6,724,522 B2 | 4/2004 | Hartung |
| 6,755,648 B2 | 6/2004 | Cao |
| 6,755,649 B2 | 6/2004 | Cao |
| 6,780,010 B2 | 8/2004 | Cao |
| 6,783,362 B2 | 8/2004 | Cao |
| 6,793,490 B2 | 9/2004 | Bianchetti et al. |
| 6,799,967 B2 | 10/2004 | Cao |
| 6,809,740 B1 | 10/2004 | Weed |
| 6,814,696 B1 | 11/2004 | Chang et al. |
| 6,824,294 B2 | 11/2004 | Cao |
| 6,835,064 B2 | 12/2004 | Burtscher et al. |
| 6,880,954 B2 | 4/2005 | Ollett et al. |
| 6,890,175 B2 | 5/2005 | Fischer et al. |
| 6,910,886 B2 | 6/2005 | Cao |
| 6,926,524 B2 | 8/2005 | Cao |
| 6,929,472 B2 | 8/2005 | Cao |
| 6,932,600 B2 | 8/2005 | Cao |
| 6,940,659 B2 | 9/2005 | McLean et al. |
| 6,953,340 B2 | 10/2005 | Cao |
| 6,955,537 B2 | 10/2005 | Cao |
| 6,969,253 B2 | 11/2005 | Cao |
| 6,971,875 B2 | 12/2005 | Cao |
| 6,971,876 B2 | 12/2005 | Cao |
| 6,974,319 B2 | 12/2005 | Cao |
| 6,979,193 B2 | 12/2005 | Cao |
| 6,979,194 B2 | 12/2005 | Cao |
| 6,981,867 B2 | 1/2006 | Cao |
| 6,988,890 B2 | 1/2006 | Cao |
| 6,988,891 B2 | 1/2006 | Cao |
| 2002/0115037 A1 | 8/2002 | Cao |
| 2002/0167283 A1 | 11/2002 | Cao |
| 2002/0167605 A1 | 11/2002 | Akimoto et al. |
| 2002/0168603 A1 | 11/2002 | Cao |
| 2002/0168604 A1 | 11/2002 | Cao |
| 2002/0168607 A1 | 11/2002 | Cao |
| 2002/0172912 A1 | 11/2002 | Cao |
| 2002/0172914 A1 | 11/2002 | Cao |
| 2002/0172915 A1 | 11/2002 | Cao |
| 2002/0172916 A1 | 11/2002 | Cao |
| 2002/0172917 A1 | 11/2002 | Cao |
| 2002/0175628 A1 | 11/2002 | Coo |
| 2002/0177095 A1 | 11/2002 | Cao |
| 2002/0177096 A1 | 11/2002 | Cao |
| 2002/0177099 A1 | 11/2002 | Cao |
| 2002/0180368 A1 | 12/2002 | Cao |
| 2002/0181947 A1 | 12/2002 | Cao |
| 2002/0190659 A1 | 12/2002 | Cao |
| 2002/0190660 A1 | 12/2002 | Cao |
| 2002/0197582 A1 | 12/2002 | Cao |
| 2003/0001507 A1 | 1/2003 | Cao |
| 2003/0113684 A1* | 6/2003 | Scott ........................... 433/29 |
| 2004/0043351 A1 | 3/2004 | Logan et al. |
| 2004/0101802 A1 | 5/2004 | Scott |
| 2004/0214131 A1 | 10/2004 | Fischer et al. |
| 2005/0158687 A1* | 7/2005 | Dahm ........................ 433/29 |
| 2005/0172917 A1 | 8/2005 | Betsch et al. |
| 2005/0182561 A1 | 8/2005 | Yamada et al. |
| 2006/0013014 A1* | 1/2006 | Hayman et al. ............. 362/572 |

* cited by examiner

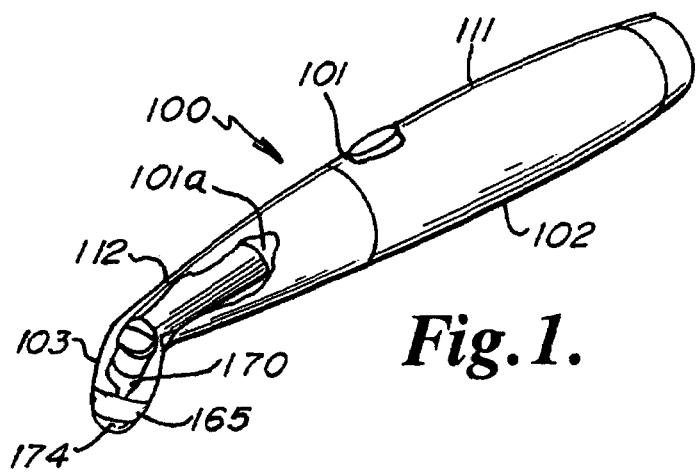
Fig.1.
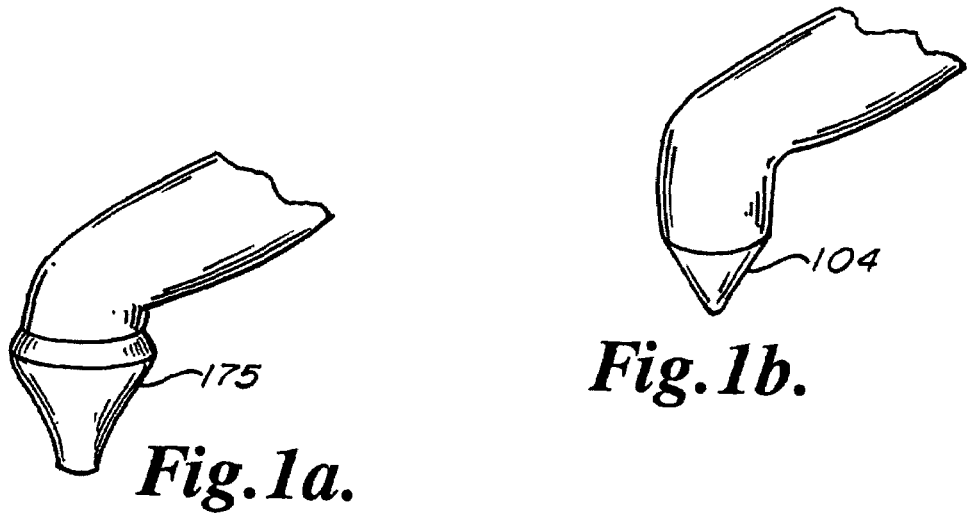
Fig.1a.
Fig.1b.

CURING LIGHT

CROSS-REFERENCE TO RELATED APPLICATIONS

This application claims the benefit of U.S. provisional patent application Ser. No. 60/585,224, filed Jul. 2, 2004, entitled "Dental Light Devices With Phase Change Heat Sink"; 60/658,517, filed Mar. 3, 2005, entitled "Apparatus and Method For Radiation Spectrum Shifting in Dentistry Application"; 60/594,297, filed Mar. 25, 2005, entitled "Curing Light Having A Detachable Tip"; 60/631,267, filed Nov. 26, 2004, entitled "Curing Light Having A Reflector"; 60/594,327, filed on Mar. 30, 2005, entitled, "Curing Light"; and 60/664,696, filed Mar. 22, 2005, entitled "Curing Light Having A Detachable Tip"; the contents of all of which are hereby incorporated by reference.

The present application includes Claims that may be related to the claims of co-pending U.S. patent applications Ser. No. 11/173,839, filed Jun. 30, 2005, entitled "Illumination System for Dentistry Applications"; Ser. No. 11/173,209. filed Jun. 30, 2005, now abandoned entitled "Voice Alert System for Dentistry Applications"; Ser. No. 11/173,371, filed Jun. 30, 2005, entitled "Support System for Dentistry"; Ser. No. 11/173,297, filed Jun. 30, 2005, entitled "Retracting Devices"; and Ser. No. 11/173,734, filed Jun. 30, 2005, entitled "Light Guide for Dentistry Applications"; the contents of all of which are hereby incorporated by reference.

FIELD OF THE INVENTION

This invention relates to curing light devices for use in dentistry. Specifically, this invention relates to curing light devices for activating the curing of composite materials in dentistry.

BACKGROUND OF THE INVENTION

In the field of tooth restoration and repair, dental cavities are often filled and/or sealed with compounds that are photosensitive, either to visible and/or ultraviolet light. These compounds, commonly known as light-curable compounds, are placed within dental cavity preparations or onto dental surfaces and are cured when exposed to light from a dental curing light device.

Many light-curing devices are configured to be handheld devices. Some of them are constructed with fiber optic light wands designed for directing light from the light sources into the patient's mouth. The light sources maybe lamps, halogen bulbs or light-emitting diodes (LED). One end of the light wand may be placed close to the light source so that the light emitted from the light source may be directed into the light wand.

Some light wands are not configured to capture all the light that is generated by the light sources, particularly light that is emitted from LEDs, which may be emitted at angles of up to about 120°. This inefficiency in capturing some of the available light output may contribute to excessive heat generation, which may lead to shorter run times for the curing devices.

One method for overcoming the limitations of light capture disclosed in the prior art is to improve the efficiency of the curing devices by placing the light source(s) of the light-curing devices at the tip of the light-curing devices, so that all of the light generated by the light source(s) may be directed towards a desired location within the patients' mouth. This, however, not only does not overcome the run time problem mentioned above, but at the same time, may create another problem of having the light source being too close to the patient's mouth, causing discomfort to the patient if the tip of the curing device happens to come in contact with the sensitive tissues of the patient's mouth.

One way of overcoming the problem of having excessive heat come too close to the patient's mouth is to mount the light source(s) on a heat sink that may generally conduct the heat away from the tip of the light-curing device. However, this only minimally solves the runtime problem mentioned above.

In addition, multiple light sources used in making a curing light capable of multiple wavelengths may further add to excessive heat generation problems if the light sources generate a wide spectrum of light, leading to more heat that needs to be diverted away from the light sources. Even with light sources generating just the desired wavelength for composite curing, heat generation is still a problem. Consequently, elaborate cooling systems are needed to handle heat, possibly creating a large, heavy and expensive curing light.

Also, for devices with multiple wavelengths, if more light intensity is generated for one wavelength as compared to a second wavelength at the same power input, unless separate power supplies are used, or power is diverted away in some fashion, the excessive intensity at one wavelength may also lead to excessive heat at the point of generation. Accordingly, there remains a need for a new device that can solve the problems listed above.

SUMMARY OF THE INVENTION

This invention relates to a dental curing light suitable for curing light curable dental composite materials. The curing light device has a light module housing having a distal end, a proximal end, a handle and a head and neck portion at the proximal end of the housing. The light module housing is of a substantially cylindrical shape having a substantially hollow interior with at least one heat sink located therein. The heat sink has at least two surfaces or mounting platforms situated at locations of at least about 180° from each other. At least two light sources, each of which may be, for example, a lamp, an arc lamp such as a halogen light source, semiconductor light emitting devices, light-emitting chips such as an LED, a solid state LED, an LED array, a fluorescent bulb, and so on, are located, positioned or mounted on the mounting platforms. The light sources emit at least two different wavelengths. The heat sink may take on various shapes, some of which may facilitate the arrangement of the light sources for a longer runtime device.

In one embodiment, the light source emitting light with a lower intensity is located closer to the proximal end of the housing.

In another embodiment, more than two light sources are present and more light sources are mounted towards the proximal end than at the distal end.

In one aspect, the light intensity of one wavelength as compared to a second wavelength at the same power input is approximately the same when the light leaves the light module housing. Thus, separate power supplies are not required, and no excessive intensity at one wavelength may lead to excessive heat at the point of generation.

The present invention also relates to a dental curing light suitable for curing light curable dental composite material with a light module housing having a distal end and a proximal end. The light module housing includes a substantially cylindrical shape defining a substantially hollow interior, a handle, a head and neck portion, with at least one heat sink located therein. The heat sink has a distal face or portion and a proximal face or portion located closer to the proximal end of the housing. At least one surface or mounting platform is located at the distal face or portion and at least one surface or mounting platform is located at the proximal face or portion of the heat sink. Located, positioned or mounted on each of the mounting platforms is a light source, as mentioned above, emitting light of a wavelength suitable for promoting cure of a composite material, with the light source mounted on the at least one mounting platform near the proximal face or portion having an output intensity lower than the light intensity emitted by the light source mounted on the mounting platform located at the distal face or portion of the heat sink.

In one embodiment, the mounting platforms located at the distal and the proximal faces or portions are oriented such that the light sources mounted on them are facing in substantially opposite directions from each other, along the longitudinal axis or off-axis of the housing, and each emitting light of a different wavelength.

In another embodiment, more than two light sources are present and are arranged in other patterns such as in a triangle, with each of the light sources closer to the proximal face or portion having a lower output intensity than each of the light sources closer to the distal face or portion.

The present invention further provides a dental curing light providing light at multiple wavelengths commonly used for restorative compounds. The curing light device includes a light module housing with an elongated heat sink located in the light module. The light module housing has a distal end, a proximal end and a substantially hollow elongated space therebetween, with the proximal end of the elongate heat sink being situated closer to the proximal end of the housing, and at least two surfaces or mounting platforms located towards the proximal end of the elongated heat sink, and at least one surface or mounting platform located towards the distal end of the elongated heat sink.

In one embodiment, located, positioned or mounted on each of the mounting platforms is a light source, as exemplified above, emitting light at a wavelength suitable for promoting cure of a composite material. The light source is located, positioned or mounted on at least one mounting platform located near the distal end of the heat sink having an output intensity higher than the light intensity emitted by each of light sources mounted on the mounting platforms located at the proximal end of the elongated heat sink. This serves to minimize the heat at the proximal end of the light-curing device and to increase the run time of the device.

In another embodiment of the invention, the at least two mounting platforms towards the proximal end of the elongated heat sink are arranged so that the light paths overlap to produce an enhance intensity of light output.

In a further embodiment, the light sources emitting different wavelengths are pointing in opposite directions, thus heat being generated tends not to be concentrated around one spot to be dissipated.

In yet a further embodiment, each of the light sources is formed on or attached to a primary heat sink which is mounted to a respective mounting platform on the elongated heat sink, the primary heat sinks being smaller in overall volume than said elongate heat sink.

In yet another embodiment, at least one reflector is formed on or attached to at least one light source located in the mounting platforms at the distal end of the heat sink. In one aspect, the reflector may be, for example, of a parabolic shape, capable of directing the light emitted by the light source towards the proximal end or head and neck portion of the light module housing. In another aspect, the mounting platform may include a reflecting surface. In a further aspect, the reflecting surface may include multiple sections adapted for capturing substantially all the light emitted by the light source located or positioned at the mounting platform at the distal end of the heat sink.

In still a further embodiment, the reflector includes a heat sink.

In still yet a further embodiment, the elongated heat sink has a well having side walls, with the proximal end being at the top of the well and the distal end at the bottom of the well.

In one aspect, the side walls have reflecting properties. In another aspect, the mounting platforms at the proximal ends of the heat sink have primary heat sinks.

The present invention additionally relates to a dental curing light having a light module housing with an elongated heat sink located in the housing towards the proximal end of the housing. The light module housing has a distal end, a proximal end, a handle and a head and neck portion, which may also be a light guide. At least one mounting platform with at least one light source is located towards the proximal end of the elongated heat sink in substantially opposite direction to the at least one mounting platform having at least one light source located towards the distal end of the elongated heat sink.

In one embodiment, the light source mounted towards the distal end of the heat sink includes at least one reflector.

The present invention further additionally relates to a dental curing light having a light module housing with an elongated heat sink located in the housing towards the proximal end of the housing. The light module housing has a distal end, a proximal end, a handle and a head and neck portion, which may also be a light guide. The elongated heat sink has a well having side walls with the proximal end being at the top of the well and the distal end at the bottom of the well. At least two mounting platforms are located towards the proximal end of the elongated heat sink, and at least one mounting platform is located towards the distal end of the elongated heat sink. On each of the mounting platforms is mounted at least one light source. The light sources may be capable of emitting same or different wavelengths. This curing light construction may be capable of more effective heat dissipation because it may minimize the concentrating the heat produced at one location.

The heat sink of the present invention may be made of any suitable material capable of absorbing, diverting, conducting heat away from the source of generation.

In one embodiment of the invention, a heat sink may be a material that can more efficiently remove or divert heat from a curing light device when a reduced weight of heat sink material is used for better portability.

In another embodiment of the invention, the elongated heat sink is of a material that may more efficiently remove or divert heat from a light source or sources with a given weight of heat sink material when compare to a heat sink made of a solid block of thermally conductive material such as metal.

The heat sink of the present invention may be made of, for example, at least one suitable phase change material including organic materials, inorganic materials and combinations thereof. These materials may undergo substantially reversible phase changes, and can typically go through a large, if not an infinite number of cycles without losing their effectiveness.

Furthermore, the present invention relates to a dental curing light capable of emitting light of more than one wavelength suitable for curing light curable dental composite material. The curing light includes at least one wavelength transformer capable of transforming at least a portion of light emitted by a light source, as noted above, into a longer wavelength which is also suitable for curing light activatable composites.

In one embodiment, the invention includes at least one wavelength transformer with at least one absorber/emitter having at least a portion that is substantially transparent to the light incident on it, and at least one portion having a chemical capable of absorbing the incident light and emitting light having a longer wavelength. In one aspect, at least one wavelength transformer may be configured or positioned to capture substantially all of the emitted light. In another aspect, at least one wavelength transformer may be configured or positioned to capture at least a portion of the light emitted by the light source. In a further aspect, at least one wavelength transformer is stationary. In still another aspect, at least one wavelength transformer is adapted for rotation about the longitudinal axis of the light module housing.

In another embodiment, at least one wavelength transformer has at least one absorber/emitter capable of absorbing all incident light and emitting light having a longer wavelength.

The curing lights of the present invention may include a light transport device at the proximal end of the housing. In one aspect, the light transport device may be a light guide. In another aspect, the light transport system may comprise a focusing dome that may also be capable of varying the beam diameter of the light exiting the curing light device. In a further aspect of the invention, the light transport system may be a tacking tip. In a further aspect, the light transport device may be a positioning light guide adapted for positioning the curing light to a target.

BRIEF DESCRIPTION OF THE DRAWINGS

FIG. 1 shows a perspective view of a curing light of the present invention.

FIG. 1a shows a portion of a curing light including a tacking tip according to one embodiment of the invention;

FIG. 1b shows a portion of a curing light including a light cone according to one embodiment of the invention;

DETAILED DESCRIPTION OF THE INVENTION

Figure 1C:
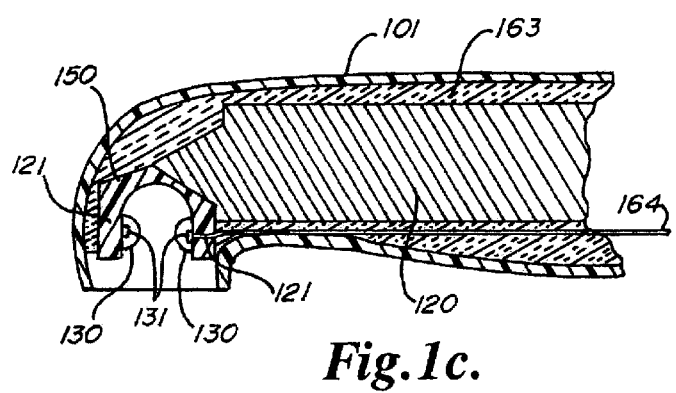
FIG. 1c shows, in cross-section, a portion of a curing light according to one embodiment of the invention.

The detailed description set forth below is intended as a description of the presently preferred device provided in accordance with aspects of the present invention and is not intended to represent the only forms in which the present invention may be practiced or utilized. It is to be understood, however, that the same or equivalent objectives and functions may be accomplished by different embodiments and components that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

A curing light device useful for curing or activating light-activated materials is disclosed. The present invention has applications in a variety of fields, including but not limited to medicine and dentistry, where light-activated materials comprising a photoinitiator or photoinitiators are used. As an example, a photoinitiator absorbs light of a particular wavelength and initiates the polymerization of monomers into polymers.

In an exemplary embodiment, light-activated materials comprising a single photoinitiator or multiple photoinitiators may be applied to a surface, such as a tooth surface, and later cured by light of a wavelength or wavelengths that activates or activate the photoinitiator or photoinitiators. The light used is not only of a wavelength to which the photoinitiator is sensitive, but also of a power level adapted to cause curing over certain durations of time. Although the light used to activate the photoinitiator is of a wavelength to which a photoinitiator is sensitive, the light may come from a variety of sources, for example, a lamp, an arc lamp such as a halogen light source, semiconductor light emitting devices, light-emitting chips such as an LED, a solid state LED, an LED array, a fluorescent bulb, and so on. Further for example, the present invention comprises light sources including semiconductor chips, LED dies, solid state LEDs, LED arrays, or combinations thereof. The light source may include an emitting surface or at least one emitting edge as in the case of an edge emitting chip noted above, for a compact curing light device.

The typical sensitizers used in composite curing include Camphorquinone (CQ), which absorbs at about 465 nm and phenyl-propanedione (PPD), which absorbs at about 390 nm. Dental curing lights having multiple wavelengths suitable for curing curable composites usually comprise output wavelengths encompassing both of the absorbing wavelengths of these two typically used photo-initiators. The output wavelengths generally include a composite spectrum generated by LEDs or LED arrays emitting different wavelengths. The present invention comprises a curing light capable of curing all typical dental composites using, for example, light sources mentioned above, including semiconductor chips, LED dies, solid state LEDs, LED arrays, or combinations thereof, mounted on mounting platforms configured on at least one heat sink.

FIG. 1 shows a curing light 100 of the present invention, including a light module housing 101 having a distal end 111, a proximal end 112, a handle 102 towards its distal end and a neck and head portion 103 on its proximal end at an angle to the handle portion 102. The light module housing 101 includes a substantially cylindrical shape having a substantially hollow interior 101a with at least one heat sink 120 located in the light module housing 101. The heat sink 120 has a longitudinal axis, or may be of any configuration adapted to promote effective thermal management within the curing light 100. In one embodiment the head and neck portion 103 may also include a light guide, such as the internal light guide 170 shown in FIG. 1. In other embodiments, as will be discussed below, the curing light includes an external light guide.

A lens cover 165 may be located towards the proximal end of the light module housing 101. In one embodiment, the lens cover 165 may be a focusing device, and may include a focusing lens or dome 174 for focusing the light towards a target surface. The focusing dome or lens 174 may also act as a device for modifying the footprint or varying the diameter of the light beam exiting the proximal end 112 of the housing 101, in order to more correctly direct the beam of light, either at a small target area or over a wider target area.

Referring now to FIG. 1a, in another embodiment, the lens cover may include a tip, such as a tacking tip 175, for molding, shaping or compacting the curable composite. The tacking tip may be a discrete attachment adapted to be coupled to the lens cover 165, as shown in FIG. 1d. In yet another embodiment, the tacking tip may be integral to the lens cover.

In one embodiment, the light guide may also be a light shield, for reducing the incidence of light generated by the light sources on human eyes and skin. In another embodiment, the light guide 170 may be configured as a lens or a focusing cone 104 for modifying the footprint or the diameter of the beam of light emitted by the light, as shown in FIG. 1b.

Figure 1D:
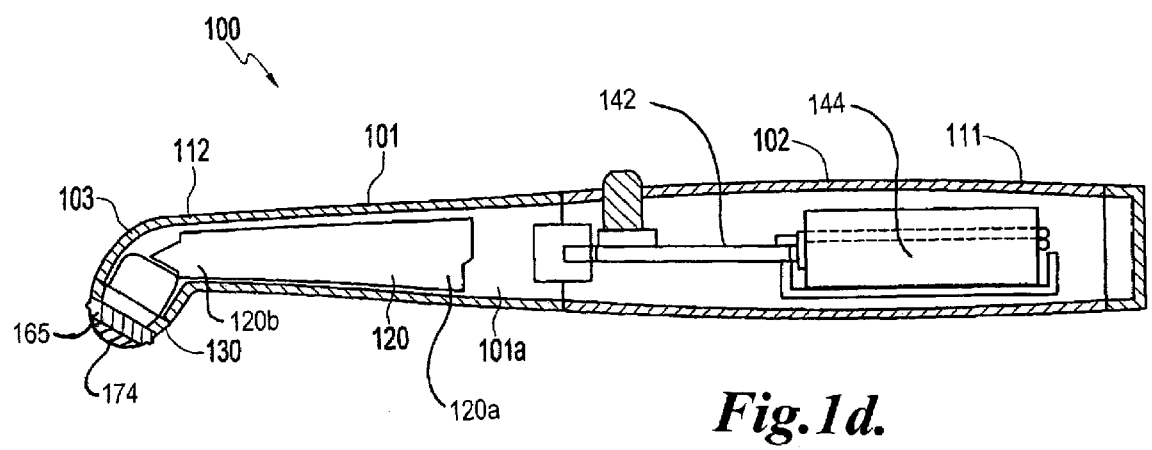
FIG. 1d shows a cross-sectional view of a curing light according to one embodiment of the invention.

In FIG. 1c, the light module housing 101 includes a substantially hollow interior with at least one heat sink 120 located in it. The heat sink 120 has at least two surfaces or mounting platforms 121 for locating, positioning or mounting light sources 130. In one embodiment, a mounting surface of the mounting platform 121 may be planar, or may have a curvature and/or surface texture. As shown in FIG. 1d, the light module housing also houses and protects, for example, electronic circuits 142 and a DC battery pack 144.

Figure 3:
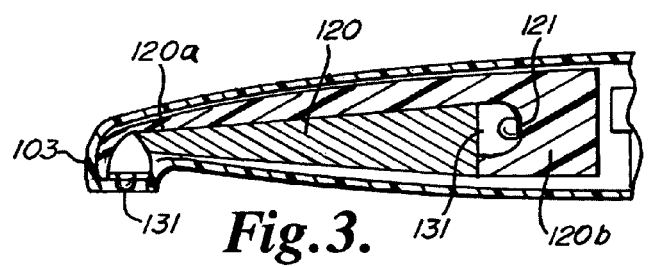
FIG. 3 shows a cross-sectional view of another embodiment of the invention, highlighting an arrangement of the mounting platforms.

In a further embodiment, each of the light sources 130 includes a light emitting diode (LED), or an LED array (as shown in FIG. 3) 131. Each of the LED's (or LED arrays) emits light useful for initiating curing of a light activated material. In one embodiment, the combined light sources 130 emit light of multiple wavelengths for activating a photoinitiator or multiple photoinitiators.

Referring again to FIG. 1c, one embodiment may include an elongated heat sink 120 having a distal end 120a and a proximal end 120b. The heat sink 120 may be located in the light module housing 101 with the proximal end 120b being situated closer to the proximal end 112 of the housing 101. The heat sink 120 may also be in any other shape. At least one surface or mounting platform 121 may be located at the distal end 120a, and at least one mounting platform 121 may be located at the proximal end 120b of the elongated heat sink 120. When other shapes of the heat sink are included in the invention, then the mounting platforms may be located at the proximal or distal surface or portion.

Mounted on each of the mounting platforms 121 is a light source 130. The light source is, for example, LEDs or an LED array 131. The light source mounted on the mounting platform 121 near the distal end 120b may have an output intensity higher than the light intensity emitted by the light source mounted on the mounting platforms 121 at the proximal end 120a of the elongated heat sink 120. The mounting platforms located at the distal and the proximal ends 120b and 120a are oriented such that the light sources 131 mounted on them are facing in substantially opposite directions from each other. In other words, they are mounted facing face to face. This may decrease the concentration of heat generation in one location. In one embodiment, the light sources are located towards the proximal end of the housing 101, so that they are close to the target area. In another embodiment, the device is fitted with a light guide 170 to keep one or more of the light sources away from the target.

Figure 2:
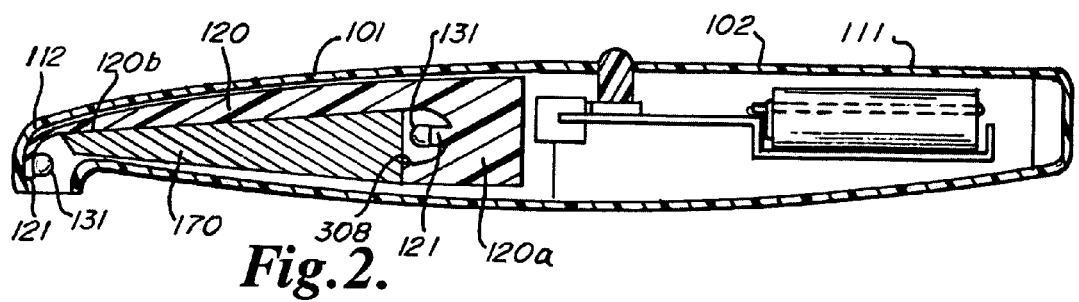
FIG. 2 shows a cross-sectional view of one embodiment of the invention, including a proximally mounted light source and a distally mounted light source.

FIG. 2 shows a curing light device of the present invention comprising a light module housing 101 with an elongated heat sink 120 located in the light housing module 101 towards the head and neck portion 103. The light module housing 101 has a distal end 111, a proximal end 112 and a substantially hollow elongated space therebetween, with the proximal end 120a of the elongate heat sink 120 being situated close to the proximal end 112 of the housing 101. The light module housing 101 also comprises a handle 102 at an angular orientation to the head and neck portion 103, to facilitate positioning at a target, especially in a limited space. At least two mounting surfaces or platforms 121 may be located towards the proximal end 120a of the elongated heat sink 120, and at least one surface or mounting platform 121 may be located towards the distal end 120b of the elongated heat sink 120. The light sources may be positioned or configured at any angular relationship to each other, such as a triangular arrangement such as at the vertices of an equilateral triangle, or back to back configuration, as shown in FIG. 3.

In one embodiment, each of the light sources towards the proximal end of the housing emits light of a lower intensity than the light source towards the distal end of the housing, to minimize the heat generated at the head and neck portion 103. This arrangement may lead to longer run time of the device.

Figure 4:
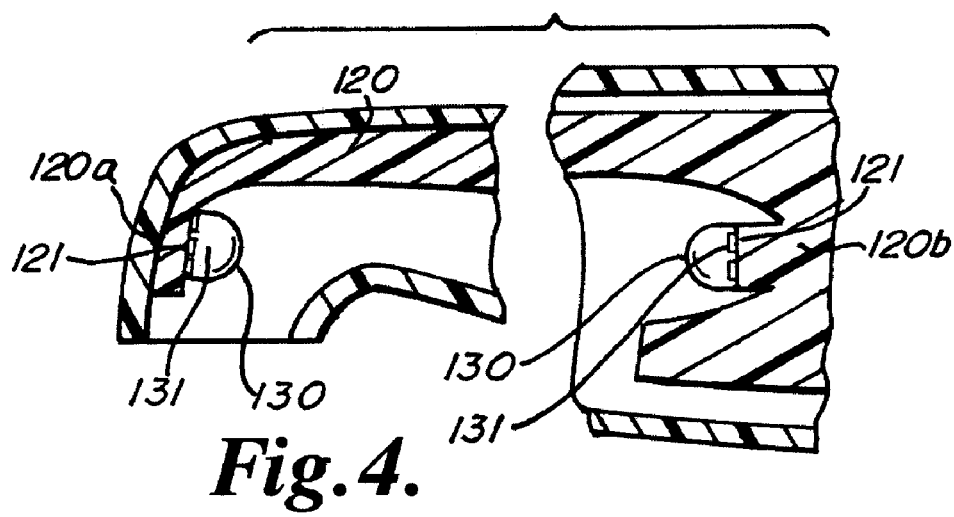
FIG. 4 shows, in cross-section, a portion of a curing light having a plurality of LED array light sources according to one embodiment of the invention.

Referring again to FIG. 2, each of the light sources 131 as shown comprises an LED. In FIG. 4, each of the light sources 131 is depicted as an LED array.

As noted, the heat sink 120 may be of any shape, as desired, for rapid heat dissipation or transfer away from the light sources 130. The light source 130 may also be any one of those mentioned above, emitting light at a wavelength suitable for promoting cure of a composite material, with the light source 130 positioned or mounted on the at least one mounting platform located near the proximal end, face or portion 120a having an output intensity higher than the light intensity emitted by the light source mounted on the mounting platforms located at the distal end, face or portion 120b of the heat sink 120.

Figure 4A:
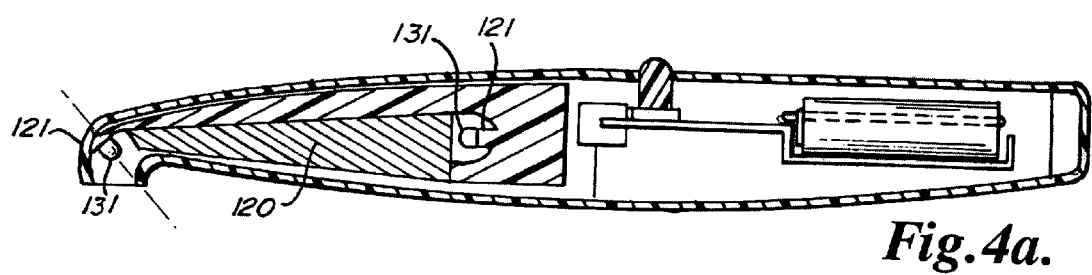
FIG. 4a shows, in cross-section, a curing light having first and second light sources with respective non-parallel optical axes.
Figure 4B:
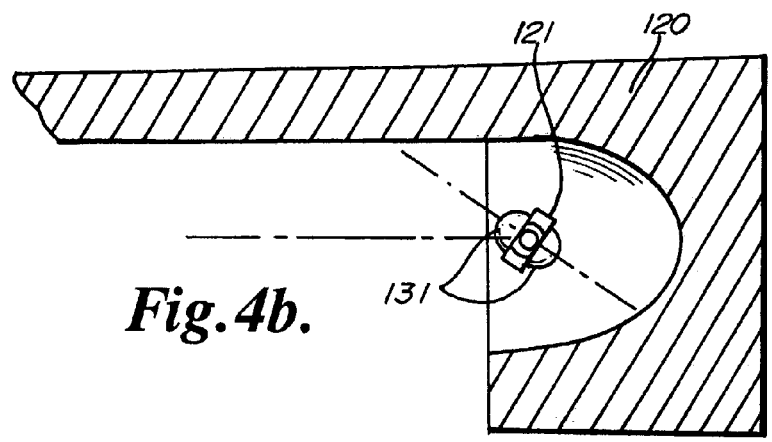
FIG. 4b shows, in cross-section, a portion of a curing light including first and second light sources with a mutual optical axis disposed non-parallel to a longitudinal axis of the curing light.

In one embodiment, the surfaces or mounting platforms 121 located at the distal and the proximal ends, faces or portions are oriented such that the light sources 130 mounted on them are facing in substantially opposite directions from each other, as shown in FIGS. 1a, 2, 3 and 4. The surfaces or mounting platforms 121 may be substantially along the longitudinal axis of the housing, as shown in FIGS. 1a, 2, 3 and 4. They may also be off-axis to the longitudinal axis of the housing 101, at any angular arrangement, as shown, for example in FIG. 4a. They may also be in off-axis arrangements, as shown in FIG. 4b. The off-axis arrangements have the added advantage that the LEDs or LED arrays may be mounted back to back, or in the same direction.

Figure 5:
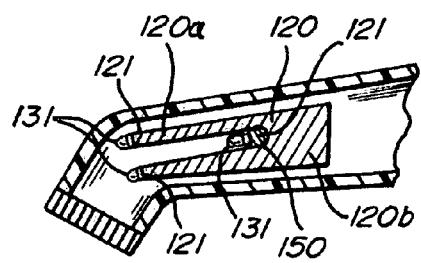
FIG. 5 show the portion of the curing light according to one embodiment of the invention including a light source disposed within a deep well.

In FIG. 5, an exemplary embodiment of an elongated heat sink 120 has a curved structure, for example a well or depression, so as to position a light source such as an LED or LED array 131 at its distal end 120b, to diffuse the concentration of heat generation.

FIG. 5 depicts a cross-sectional view of an elongated heat sink 120 having a deep well having side walls with the proximal end 120a being at the top of the well and the distal end 120b at the bottom of the well. At least two mounting platforms 121 may be located towards the proximal end 120a, and at least one mounting platform 121 may be located towards the distal end 120b of the elongated heat sink. On each of the mounting platforms 121 may be mounted at least one LED 131. The LED 131 may be capable of emitting same or different wavelengths. The light sources 131 may be capable of emitting the same or different wavelengths. This curing light construction is capable of more effective heat dissipation by not concentrating the heat product at one location.

Figure 5A:
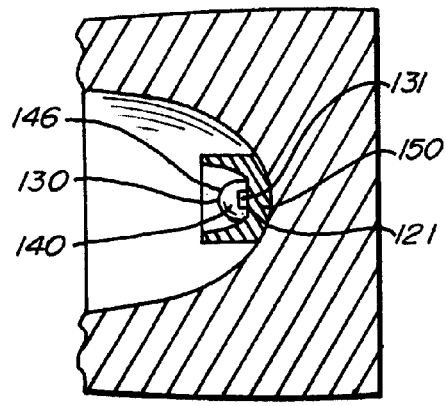
FIG. 5a shows a portion of a curing light according to one embodiment of the invention including a local reflector disposed about a light source.

As shown in additional detail in FIG. 5a, at the distal end 120b, there may be a smaller primary heat sink 150 or an LED having a smaller primary heat sink 150 mounted thereon. At the distal end 120b, there may be a smaller primary heat sink 150 or an LED having a smaller primary heat sink 150 mounted thereon. The smaller primary heat sink may also comprise a well, which may also act as a reflector if it includes a reflecting surface, to reflect all stray light towards the target area.

The elongated heat sink 120 as shown may also have a planar mounting platform 121 on its distal end (not shown) for mounting light sources such as LEDs or arrays 131, or the platform may include a reflector.

Heat management is important, especially for a compact and/or hand held curing light. If heat transfer and dissipation are not handled adequately, damage to the LEDs or LED arrays may result, or light output of the LEDs or LED arrays may be diminished or compromised.

Different geometric shapes facilitate the arrangements of the light sources for improved runtime efficiency. This along with higher efficiency heat sinks may lead to a better curing light.

Though the heat sink 120 is shown as an elongated shape, it may also be of other shapes, as desired, for rapid heat dissipation or transfer away from the light sources such as the LEDs or LED arrays 131 shown in FIGS. 1a, 2 and 4.

Figure 7:
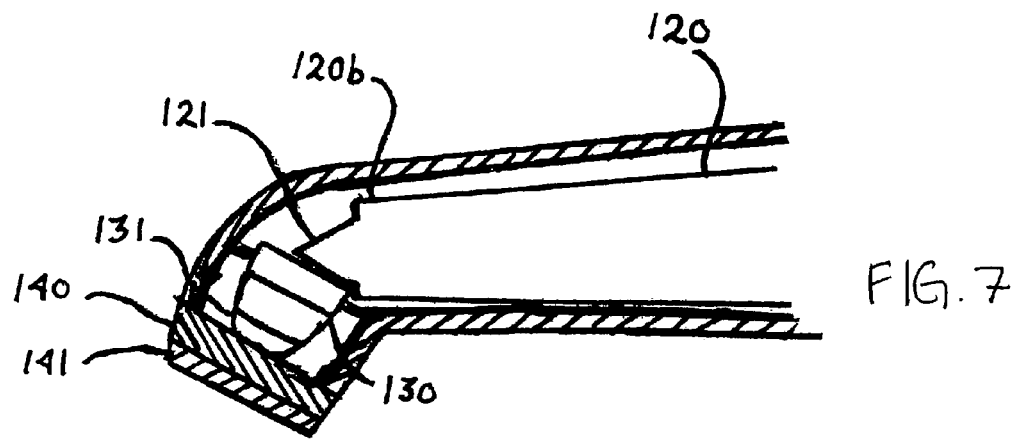
FIG. 7 shows a curing light having a wavelength transformer according to one embodiment of the invention.

In addition, the LED or LED array 131 maybe covered by a protective cover or dome or a focus lens 174, as mentioned above. In one embodiment, the protective cover, dome or focus lens may also include a wavelength transformer 140, as shown in FIG. 7, for transforming low wavelengths unsuitable for curing composites into a longer wavelength suitable for use. This can potentially improve the efficiency of the system and decrease the amount of heat needed to be diverted or conducted away from the light sources 130.

The wavelength transformer 140 includes at least one absorber/emitter. The absorber/emitter may be any substance that may be used for absorbing the electromagnetic waves, for example, in the blue wavelength range, and then luminesce, in particular fluoresce, when optically excited. Such chemical compounds may include organic and inorganic dyes or pigments.

In one embodiment, the wavelength transformer 140 may include a substrate; at least one absorber/emitter matrix capable of absorbing a first shorter wavelength of light and transforming or re-emitting that light at a longer wavelength; and a cover element. In another embodiment, the wavelength transformer may be positioned at any distance from an emitting surface, from a few μm to a few mm, including right at the light source or emitting surface or edge, or incorporated therewith into the construction of the emitting surfaces or edges. Such incorporation of the absorber/emitter may be accomplished by sputtering, thin film deposition, vapor deposition, lithographic printing, coating, or other techniques known in the art. In yet another embodiment, the wavelength transformer may include portions of the light source or the protective cover of the light source. In still a further embodiment, the wavelength transformer may also include a beam splitter (not shown). Examples of the wavelength transformer and the types of absorber/emitter are disclosed in U.S. Provisional Application No. 60/658,517 filed Mar. 3, 2005, incorporated herein by reference.

The wavelength transformer 140 includes at least one absorber/emitter 141 having at least a portion that is substantially transparent to the incident light, and at least one portion capable of absorbing the incident light and emitting light having a longer wavelength. In one embodiment, at least one wavelength transformer may be configured or positioned to capture substantially all of the emitted light while transforming only a portion of the capture light into a longer wavelength.

In another embodiment, at least one wavelength transformer including an absorber/emitter may be configured or positioned to capture at least a portion of the light emitted by the light source and transforming all captured light. The absorber/emitter 141 may be positioned at any distance away from an emitting surface, from a few μm to a few mm.

For an absorber/emitter capable of capturing all of the emitted light and transforming only a portion of it into a longer wavelength, the dye, pigment or mixtures thereof, may be present in at least at portion of the absorber/emitter. In one embodiment, the absorber/emitter has a matrix of domains including dyes, pigments or mixtures thereof, surrounded by domains that are substantially transparent to the incident light. The domains may be of any size, including domains of the size of a few molecules, to domains that may be almost half the size of the entire absorber/emitter. In another embodiment, the configuration of the absorber/emitter may have two separate portions, one portion including a dye, pigment or mixtures thereof, capable of absorbing a shorter wavelength and emitting a longer wavelength and the other portion being transparent to the incident light. In one other embodiment, the configuration of the absorber/emitter may have a matrix of domains of any shape and size, some of which may include a dye, pigment or mixtures thereof, capable of absorbing a shorter wavelength and emitting a longer wavelength and the others being transparent to the incident light. In a further embodiment, the configuration of the absorber/emitter may have a matrix of stripes having a dye, pigment or mixtures thereof, interposed with stripes of having no dye or pigment. The coating of dye, pigment or mixtures thereof may be deposited in a variety of patterns including, straight line patterns such as parallel longitudinal lines, parallel transverse lines; rectangular patterns; circular or arcuate patterns; dot patterns such as symmetrical or unsymmetrical patterns of dots, and combinations thereof. The patterns may be formed by any of a number of coating methods including slot coating, pattern coating, and rotogravure coating and the like. Suitable methods for applying selected patterns include, for example, slot coating, transfer coating, and rotogravure coating, may be used.

For the absorber/emitter capable of capturing at, least a portion of the emitted light and transforming substantially all of the captured light into a longer wavelength, the dye, pigment or mixtures thereof may be present in substantially all regions of the absorber/emitter.

Examples of materials useful as an absorber/emitter in a wavelength transformer may include an organic dye, pigment or mixtures thereof, as discussed in, for example, U.S. Pat. No. 5,126,214 to Tokailin et al. (which discloses a fluorescent material part that emits in a visible light range from red to blue); and U.S. Pat. No. 5,294,870 to Tang et al. (which makes reference to the use of both organic and inorganic dye materials), the contents of which are incorporated herein by reference.

For an absorber/emitter capable of capturing at least a portion of the light emitted by the light source and transforming all captured light, the absorber/emitter may have a matrix of a uniform coating or layer of a dye, pigment or mixtures thereof in its entirety.

In one aspect of the invention, at least one wavelength transformer may be fixed in the light path of the light source. In another aspect, at least one wavelength transformer is adapted for rotation about the longitudinal axis of the light module housing. In a further aspect, at least one wavelength transformer may be, for example, in the form of an interchangeable filter disk, permanently or reversibly connected to a light guide. One embodiment of a light guide.

In one embodiment, the wavelength transformer includes a substrate, an absorber/emitter matrix capable of absorbing a lower wavelength of light and transforming or re-emitting that light at a longer wavelength, and a cover element.

The dye, pigment or mixtures thereof, may be coated on any substrate such as a sheet or a plate of glass, a polymer film such as polymethylmethacrylate (PMMA), polyethylene (PE), polypropylene (PP), polystyrene (PS), polycarbonate (PC), polyvinylchloride (PVC), polyester terephthalate (PET) or combinations thereof, to form the absorber/emitter matrix.

The housing 101 may be made of any polymeric material, for example, a polymer that can be molded or cast; or a metal or metallic alloy. Suitable polymers include polyethylene, polypropylene, polybutylene, polystyrene, polyester, acrylic polymers, polyvinylchloride, polyamide, or polyetherimide like ULTEM®; a polymeric alloy such as Xenoy® resin, which is a composite of polycarbonate and polybutyleneterephthalate or Lexan® plastic, which is a copolymer of polycarbonate and isophthalate terephthalate resorcinol resin (all available from GE Plastics), liquid crystal polymers, such as an aromatic polyester or an aromatic polyester amide containing, as a constituent, at least one compound selected from the group consisting of an aromatic hydroxycarboxylic acid (such as hydroxybenzoate (rigid monomer), hydroxynaphthoate (flexible monomer), an aromatic hydroxyamine and an aromatic diamine, (exemplified in U.S. Pat. Nos. 6,242,063, 6,274,242, 6,643,552 and 6,797, 198, the contents of which are incorporated herein by reference), polyesterimide anhydrides with terminal anhydride group or lateral anhydrides (exemplified in U.S. Pat. No. 6,730,377, the content of which is incorporated herein by reference) or combinations thereof.

In addition, any polymeric composite such as engineering prepregs or composites, which are polymers filled with pigments, carbon particles, silica, glass fibers, conductive particles such as metal particles or conductive polymers, or mixtures thereof may also be used. For example, a blend of polycarbonate and ABS (Acrylonitrile Butadiene Styrene) may be used for the housing 101.

Generally, examples for the housing 101 include, for example, polymeric materials or composites having high temperature resistance.

Suitable metal or metallic alloys may include stainless steel; aluminum; an alloy such as Ni/Ti alloy; any amorphous metals including those available from Liquid Metal, Inc. or similar ones, such as those described in U.S. Pat. No. 6,682,611, and U.S. Patent Application No. 2004/0121283, the entire contents of which are incorporated herein by reference.

A liquid crystal polymer or a cholesteric liquid crystal polymer, such as one that can reflect rather than transmit light energy, may be used, for example, as a coating in the interior 101 of the light module housing 101, to minimize the waste of light energy generated by the light source, as described, for example, in U.S. Pat. Nos. 4,293,435, 5,332, 522, 6,043,861, 6,046,791, 6,573,963, and 6,836,314, the contents of which are incorporated herein by reference.

Figure 5B:
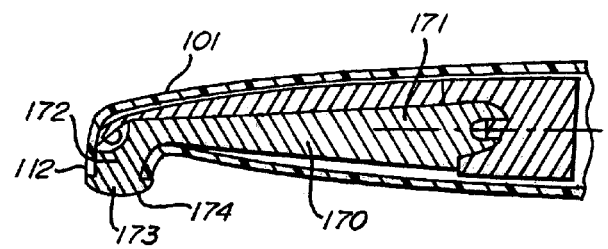
FIG. 5b shows, in cross-section, a portion of a curing light having a light guide including a cap portion.
Figure 5C:
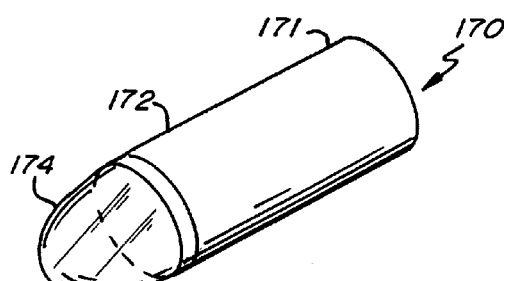
FIG. 5c shows a light guide including a cover.

The use of a light transport device such as a light guide 170, as shown for example in FIG. 1, may be a means of keeping heat away from the target surface and its surroundings, such as a patient's mouth. The light guide also helps to diffuse, rather than concentrate heat generated. The light guide 170 may have an elongate shape, as shown for example in FIG. 2, and may be in the form of a substantially hollow tube, a pipe or an optically conductive cable, having a distal end 171, attached to the distal end 112 of the light module housing 101, and a proximal end 172 having a cover 173 (as shown, e.g., in FIG. 5b). Alternately, a cover 173 may be fitted over the proximal end 172 of the light guide 170. The cover may include a focusing dome, or lens 174 for focusing the light towards the target surface, such as shown in FIG. 5c. This cover may also include a wavelength transformer, as noted before, for transforming any unsuitable lower wavelength light into wavelengths that are suitable for use. In one embodiment, the cover 173 is removable and may be replaced with a tip, such as a tacking tip 175, as shown in FIG. 1a, for molding, shaping or compacting the curable composite. In another embodiment, the focusing dome or lens 174 may also act as a device for varying the size of the light beam exiting the proximal end 112 of the housing 101, in order to more correctly direct the beam of light, either at a small target area or over a wider target area. The varying diameter feature may be done by means of different focusing domes or lens 174, or a dome or lens 174 may include an adjusting mechanism to vary the beam diameter, as shown for example in FIG. 5c.

In the embodiment as shown in FIG. 1, the head and neck portion 103 may include a light guide 170, wherein the light source or sources are present towards the distal end of the handle 102, for transporting light towards a target. In one embodiment, and the light source or sources are mounted inside the head and neck portion 103, at the proximal end of the handle 102.

Figure 8A:
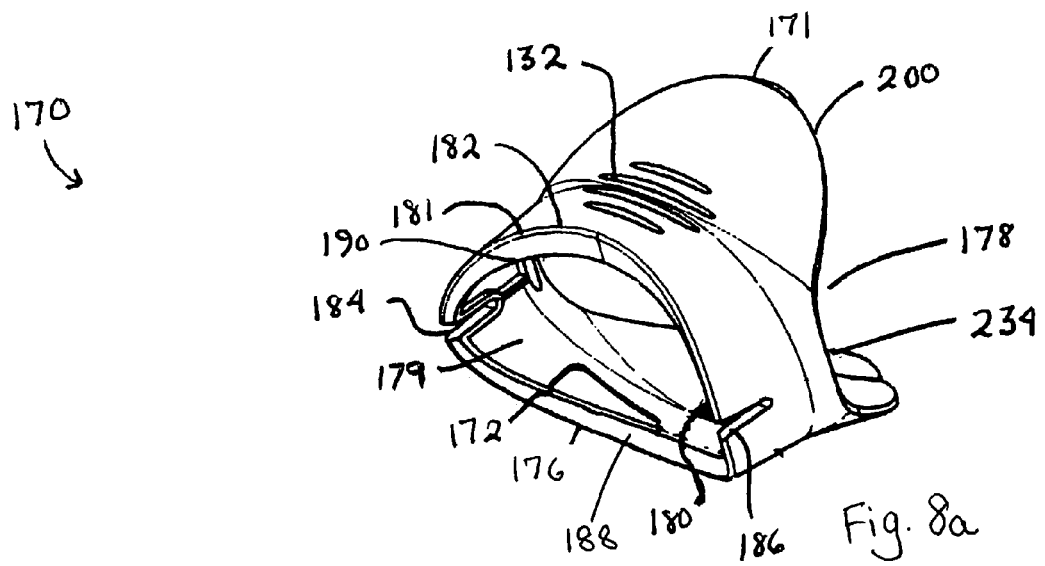
FIG. 8a shows an embodiment of a light guide according to one embodiment of the invention.

In another embodiment of the invention, a supporting light guide 189 serves to help position the curing light, is shown in FIG. 8a.

The light guide 170, as shown in FIG. 8a, includes an elliptically tubular member having an axial cavity 179 disposed between a front aperture 176 and a rear aperture 178. As shown in the illustrated embodiment, a first edge 181 of the tubular member defines a substantially elliptically saddle shaped curve having a convex form in relation to a generally horizontal portion 180 thereof and a concave form in relation to a generally vertical portion 182 thereof. In addition, edge 181 includes first and second substantially horizontal slots 184, 186. According to one embodiment of the invention, the slots 184, 186 are disposed substantially coplanar with respect to one another and are disposed substantially coincident with a major axis of the elliptically saddle shaped curve that defines edge 181.

As shown in the illustrated embodiment, a rim 188 extends radially inwardly from the edge 181 to a second substantially elliptically saddle shaped curved edge 190 (also referred to as the "second edge"). The second edge 190 is disposed in substantially constantly space relation to edge 181, whereby the rim 188 has a substantially uniform radial dimension over the length of edge 181. Edge 190 defines an outer periphery of the front aperture 186.

At the rear end of the embodiment of FIG. 8a, a third edge 200 defines another curve that is of an approximately elliptically saddle shape. Edge 200 may be substantially concave in form in relation to a generally horizontal portion 132 thereof and is generally convex in form in relation to a generally vertical portion 234 thereof. The detailed description of the light guide is found in U.S. Provisional Patent Applications No. 60/641,468 and 60/647,580; Co-pending U.S. patent application entitled "Light Guide for Dentistry Applications", to be filed concurrently with this case, and U.S. Design Patent Application No. 29/220,680 incorporated herein by reference in their entirety.

Figure 8B:
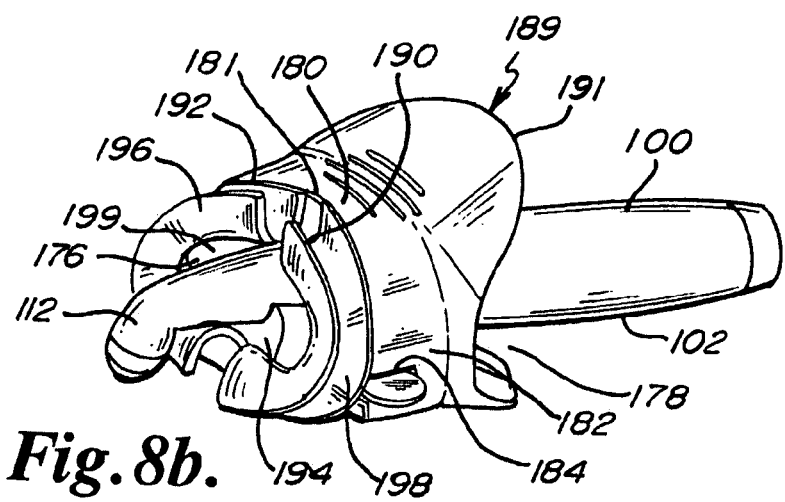
FIG. 8b shows an embodiment of a curing light with a positioning light guide according to one embodiment of the invention.

According to the embodiment as shown in FIG. 8b, the supporting light guide 189 includes a distal end 191 and a proximal end 192. In one exemplary embodiment, the proximal end 192 of the light guide 189 may be adapted to be coupled to a support structure 194 disposed at a proximal end 112 of the housing 102. In another embodiment, the distal end 191 of the light guide may include at least one formation adapted to be coupled to a curing light 100 and the proximal end 192 of the light guide may include at least one other formation adapted to be coupled to a lip retracting device 196.

The lip retracting device 196 includes a surface 198 adapted to support the lips of a subject patient. The lip retracting device includes at least one formation, such as a wing-like member, for coupling to the at least one formation of the light guide. In use, the lip retracting device serves to draw the soft tissue of the lips away from the teeth of the patient so as to provide and un-obstructed optical path between the proximal end of the light guide and a tooth surface of the subject patient. The lip retracting device is described in U.S. and patent application No. 60/641,461, as well as a co-pending U.S. patent application entitled "Retracting Devices", to be filed concurrently with this case, the contents of which are incorporated herein by reference.

The light guide 189 as shown includes an elliptically tubular member having an axial cavity 199 disposed between a front aperture 176 and a rear aperture 178. As shown in the illustrated embodiment, a first edge 181 of the tubular member defines a substantially elliptically saddle shaped curve having a convex form in relation to a generally horizontal portion 180 thereof and a concave form in relation to a generally vertical portion 182 thereof. In addition, edge 181 includes first and second substantially horizontal slots, e.g., 184. According to one embodiment of the invention, the slots, e.g., 184 are disposed substantially coplanar with respect to one another and are disposed substantially coincident with a major axis of the elliptically saddle shaped curve that defines edge 181.

As shown in the illustrated embodiment, a rim 188 extends radially inwardly from the edge 181 to a second substantially elliptically saddle shaped curved edge 190 (also referred to as the "second edge"). The second edge 190 is disposed in substantially constantly space relation to edge 181, whereby the rim 181 has a substantially uniform radial dimension over the length of edge 181. Edge 190 defines an outer periphery of the front aperture 186.

The light guide 189 may be made of similar material as that of the light module housing 101 as described above. Also, biodegradable or biocompostable polyesters such as a polylactic acid resin (comprising L-lactic acid and D-lactic acid) and polyglycolic acid (PGA); polyhydroxyvalerate/hydroxybutyrate resin (PHBV) (copolymer of 3-hydroxy butyric acid and 3-hydroxy pentanoic acid (3-hydroxy valeric acid) and polyhydroxyalkanoate (PHA) copolymers; and polyester/urethane resin may also be suitable, especially if the light guide is to be a single-use device.

Additionally, like the light module housing 101, a cholesteric liquid crystal polymer, one that can reflect rather than transmit light energy, may be used, either as a coating or as the main ingredient of the light guide to minimize escape of light energy, as described, for example, in U.S. Pat. Nos. 4,293,435; 5,332,522; 6,043,861; 6,046,791; 6,573,963; and 6,836,314, the contents of which are incorporated herein by reference.

Also, the structure of the light guide, for example, may include a UV-inhibiting material in order to protect the patient's skin from ultra-violet light exposure.

Figure 9:
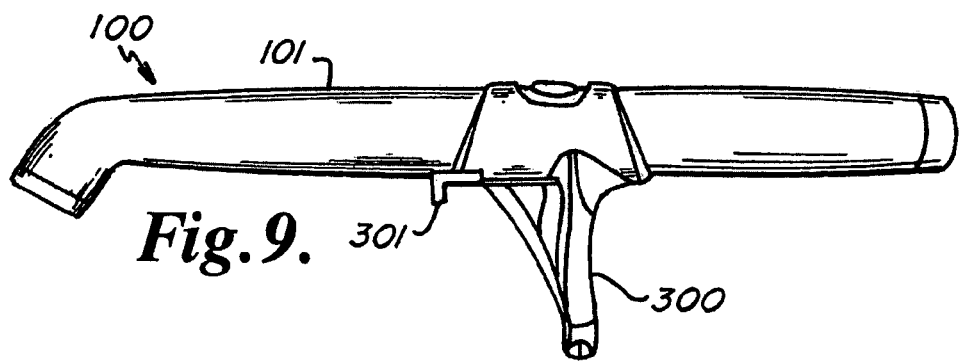
FIG. 9 shows a curing light including a handgrip according to one embodiment of the invention.

In one embodiment, as shown in FIG. 9, the handle 102 of the curing light may be fitted with a hand grip device 300 having a coupler 301, for coupling the curing light to the light housing 101.

In another embodiment, the handle 102 of the curing light may also be rested on the horizontal portion of the positioning light guide structure during use to help support the curing light. The positioning light guide may also help to fix the spatial relationship between the light source and the target area, so that any accidental movement by the operator does not also result in the curing light being pointed in an undesirable location.

Referring again to FIG. 2, a reflector 308 for reflecting portions of the emitted light is depicted. In one embodiment, as shown, the reflector includes an inner surface of the heat sink 120. In another embodiment, a reflective coating is disposed on the inner surface of the heat sink 120.

The reflector is mounted towards the distal end, face or portion of the heat sink, for reflecting light emitted by the light source, such as an LED (as shown in FIG. 1a or 2) or an LED array (FIG. 4) 131 towards the proximal end 112 of the housing 101. The reflector helps to direct the light beam in the desired direction and also helps to ensure that light energy is not wasted.

Figure 6:
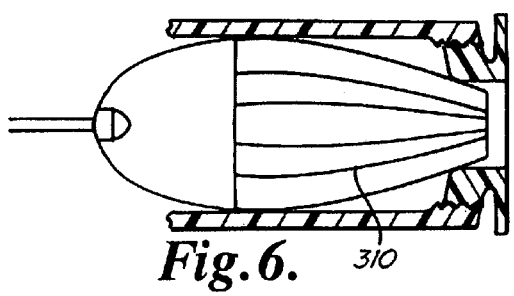
FIG. 6 shows a portion of a curing light having a petal reflector according to one embodiment of the invention.

The reflector may also include multiple petals 310, as shown in FIG. 6. The movement of the petals, such as opening and closing may collect light form a wider or smaller area. This type of reflector may also help to vary the size of the beam.

Figure 10:
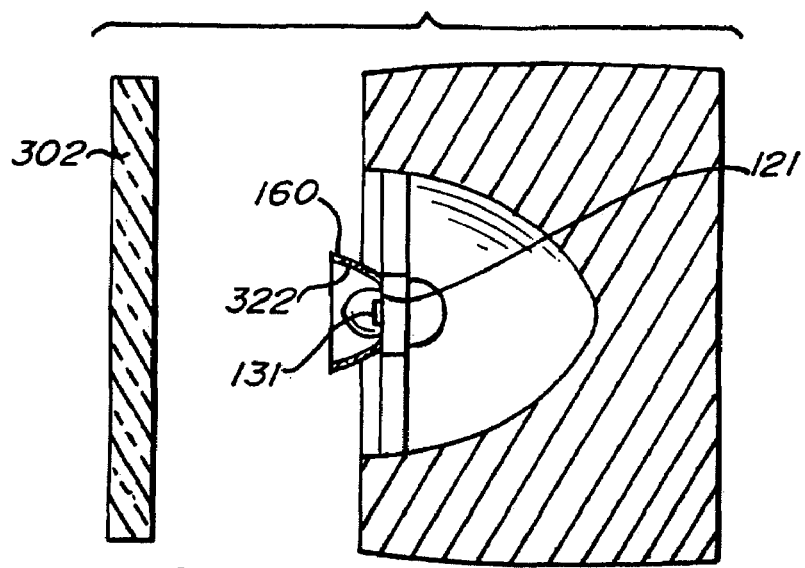
FIG. 10 shows a curing light having a wavelength transformer according to one embodiment of the invention.

In other embodiments, as shown in FIG. 10, the inside surface 101a of the light module housing 101 may include reflecting surfaces, adapted also for reflecting and directing substantially all stray light emitted by the LED 131 towards the proximal end 112 of the light module. At least one wavelength transformer 140 may be positioned in the path of the light coming both from the LED and the reflector.

In one aspect, the reflecting surface is present towards the proximal end 112, near the head and neck portion 103 of the housing 101. In another aspect, the reflecting surface may be present substantially in most of the interior of the proximal end 112 of the light module housing.

The reflector may include an opening through which light passes.

In various embodiments, the reflecting surface of either a discrete reflector 160, the curved walls of a heat sink 120, or the interior 101a of housing 101, may include, for example, a reflective metal, a highly polished metal, or a non-specular paint. A reflective metal, for example, a metal having a reflectivity greater than 90%, may improve the yield of light collected by the curing light by, for example, approximately 50%. Examples of suitable metals include silver, aluminum, rhodium, and gold. The reflective metal may also be selected based on, for example, the substrate the reflective layer is to be deposited, or the wavelength of the light it is to reflect. For example, it is known that gold is highly reflective of light in the red or infra-red wavelength ranges.

In other embodiments, the reflecting surfaces include anodized aluminum, and surfaces formed by vapor deposition of dielectric layers onto metallic layers, or polymeric layers. For example, in one embodiment, a metallic layer is disposed on an anodized surface as a base reflection layer. This is followed by deposition of a low refractive index and then a high refractive index dielectric layer. Suitable materials for these layers include those available from Alanod, Ltd. of the United Kingdom.

The reflector 160 may also include a highly polished metal. Additional embodiments of the reflecting surfaces include anodized aluminum, and surfaces formed by vapor deposition of dielectric layers onto metallic layers, or polymeric layers. For example, in another embodiment, a metallic layer is disposed on an anodized surface as the base reflection layer, followed by deposition of a low refractive index and then a high refractive index dielectric layer. Again, suitable materials for these layers include those available from Alanod, Ltd. of the United Kingdom.

In addition, the reflector 160 may also include a liquid crystal polymer plastic, one that can reflect rather than transmit light energy, either as a surface coating for the reflecting surface or as a main ingredient of the reflector 160. The liquid crystal polymer can be that as described, for example, in U.S. Pat. Nos. 4,293,435; 5,332,522; 6,043,861; 6,046,791; 6,573,963; and 6,836,314, or other materials with similar properties. Many different configurations of reflector may be employed in the invention including, for example, a parabolic reflector capable of directing the light emitted by the LED towards the proximal end of the handle.

Figure 10A:
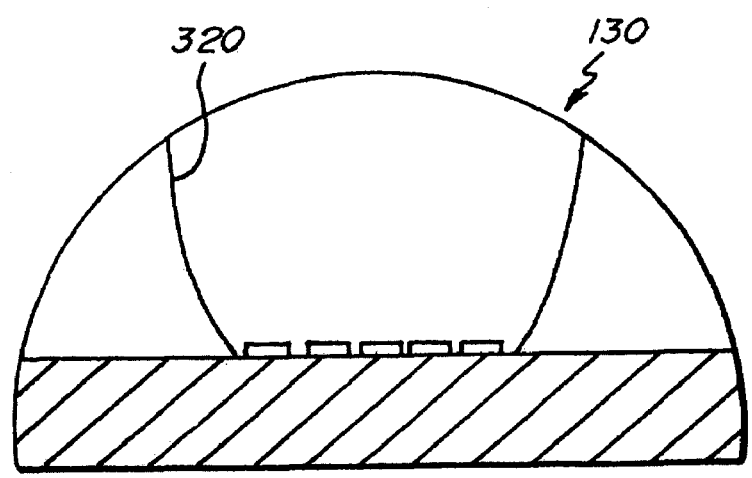
FIG. 10a shows a light source including an integral reflector according to one embodiment of the invention.

As shown in FIG. 10a, at least one reflective surface 320 may also be integral to the light source 130, either formed on or attached to it. This reflective surface 320 may be, for example, of a parabolic shape, again capable of directing the light emitted by the LED towards the proximal end of handle.

The heat sink 120 is important in thermal management in the present invention, as noted above, along with the positioning or configuration of the heat generating source. In the embodiment depicted in FIGS. 2, 3 and 4, multiple LEDs or LED arrays 131 may be mounted on the plural mounting platforms of one heat sink 120. In another embodiment of the invention, each of the LEDs or LED arrays 131 may be formed on or attached to a primary heat sink 150.

In one embodiment, as shown in FIG. 1c, at least one primary heat sink 150 is mounted to the mounting platform of a secondary heat sink, such as an elongated heat sink 120. The primary heat sink 150 may be smaller in overall volume than the secondary heat sink 120. In one embodiment of the invention, no secondary heat sink is present in addition to the primary heat sink. In yet another embodiment, the secondary heat sink may be an air gap, an air jacket, a fan circulated gas, or a combination thereof.

In still another embodiment of the invention, as shown in FIG. 10, the at least one LED located on a mounting platform 121 located towards the proximal end of the housing 101 may have a reflector 160 formed on, or attached to, it. The reflector 160 includes a surface 322 that is, for example, parabolic, or conical. The surface is adapted to reflect and direct substantially all stray light emitted by the LED 131 towards the proximal end of the handle. In one embodiment, at least one wavelength transformer 302 is positioned in the path of the light coming both from the LED and the reflector 160. This wavelength transformer 302 may be constructed in modular form, to be replaced or removed, if desired.

Figure 11:
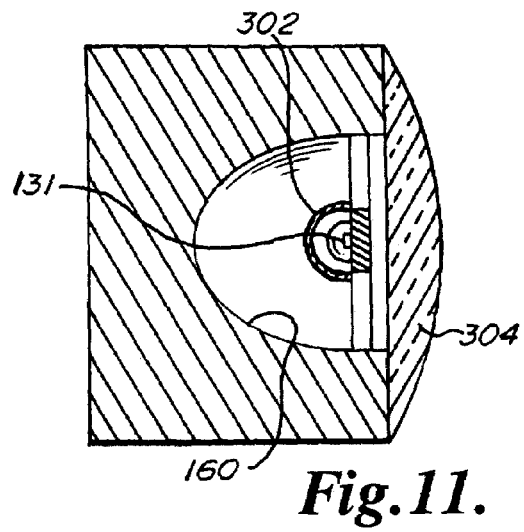
FIG. 11 shows a portion of a curing light having a wavelength transformer and a lens according to one embodiment of the invention.

As shown in FIG. 11, the light emitted by the LEDs or LED array 131 passes through at least one wavelength transformer 302 and is then collected by a reflector apparatus 160 and focused by a focusing device 304.

In other embodiments, the inside surface 101a of the light module housing 101 may include one or more reflecting surfaces, adapted also for reflecting and directing substantially all stray light emitted by the LED 131 towards the proximal end 112 of the light module. At least one wavelength transformer 302 may be positioned in the path of the light coming both from the LED and the reflector.

In one aspect, the reflecting surface is present towards the proximal end 112, near the head and neck portion 103 of the housing 101. In another aspect, the reflecting surface may include a majority of the interior surface of the proximal end 112 of the light module housing. In a further aspect, the walls of a curved heat sink, as shown in FIG. 5, may also act as a reflector.

The reflecting surface of either a reflector 160, the surfaces of a heat sink, or the interior 101a includes, for example, a highly polished metal. Other embodiments of the reflecting surfaces include anodized aluminum, and surfaces formed by vapor deposition of dielectric layers onto metallic layers, or polymeric layers, for example, a metallic layer on an anodized surface as the base reflection layer, followed by deposition of a low refractive index and then a high refractive index dielectric layer, such as those available from Alanod, Ltd. of the United Kingdom.

In addition, the reflector 160 may also include a liquid crystal polymer plastic, one that can reflect rather than transmit light energy, either as a surface coating for the reflecting surface or as a main ingredient of the reflector 160. The liquid crystal polymer can be that as described, for example, in U.S. Pat. Nos. 4,293,435; 5,332,522; 6,043,861; 6,046,791; 6,573,963; and 6,836,314, or other materials with similar properties. Also, a reflector may be formed in a variety of different configurations. For example, the reflector may include a parabolic surface, capable of directing the light emitted by the LED towards the proximal end of the handle.

At least one reflector 160 may also be integral to the light source as shown in FIG. 10, either formed on or attached to it. This reflector 160 may also be, for example of a parabolic shape, again capable of directing the light emitted by the LED towards the proximal end of handle.

As noted, the heat sink may be an elongated heat sink, but it may also be of any other appropriate shape. The primary heat sinks, if present, may be attached to the LEDs, either by integral forming such as molding, or by attachment means, such as an adhesive. The mounting platform 121 may be part of a well in the surface of the heat sink. According to one embodiment, an inwardly facing surface of the well may include a reflective surface, as shown in FIG. 5.

In one embodiment, as shown in FIG. 1c, the light module housing 101 may be separated from the heat sink 120 by a buffer layer or an insulator 163. The heat sink 120 may occupy, for example, less than about 60%, more for example, less than about 50% of the length of the light module housing 101. Electrically conductive wires 164 are also provided to power the light sources such as the LEDs or LED arrays 131. The buffer layer or an insulator 163 serves to separate the heat sink 120 from the housing 101 to facilitate the control of thermal energy. The insulator may be in the form of an insulation tape, an air space, an air jacket, or any material that will provide spacing and distance between the heat sink 120 and the light module housing 101, so as to form an air jacket and permit air circulation, ventilation and heat dissipation. The insulator may also include a rubber, a silicone, a plastic or other material, or a combination thereof.

Figure 12:
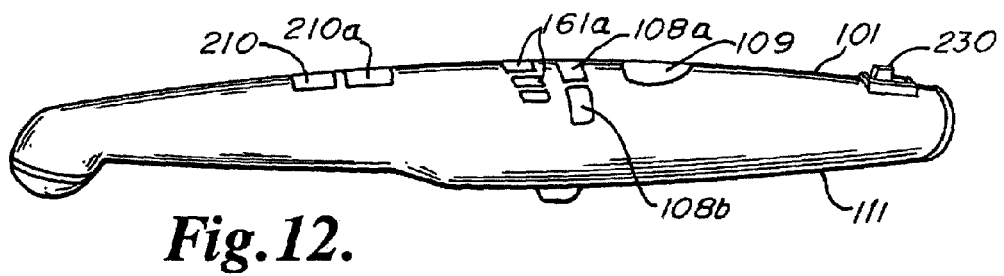
FIG. 12 shows a curing light according to another embodiment of the invention.

As shown in FIG. 12, the housing 101 may also have one or more vents or holes 161a to permit or encourage air to travel from outside the casing 101 into the air jacket 163 (as shown in FIG. 1c), and/or to permit or encourage air from the air jacket 163 to travel outside of the housing 101. This air exchange may assist in cooling the light module 100, especially during the resting or recharging cycle of the device. The air jacket 163 may thus assist in avoiding a buildup of heat in the device that could result in short run time or even cause user discomfort.

The heat sink may be made of any material that has good thermal conductivity, and/or dissipation properties, such as a metal or non-metal, for example, copper, aluminum, silver, magnesium, steel, silicon carbide, boron nitride, tungsten, molybdenum, cobalt, chrome, Si, SiO.sub.2, SiC, AlSi, AlSiC, natural diamond, monocrystalline diamond, polycrystalline diamond, polycrystalline diamond compacts, diamond deposited through chemical vapor deposition and diamond deposited through physical vapor deposition, and composite materials or compounds.

In another embodiment, the heat sink includes heat conduction pipes. In another embodiment, the heat sink 120 includes phase change materials, some embodiments and material are exemplified as is described in Ser. No. 10/XXX, XXX, a co-pending patent application, entitled "Dental Light Devices Having an Improved Heat Sink", to be filed concurrently; and a U.S. Patent Application No. 60/585,224, filed Jul. 2, 2004, entitled "Dental Light Devices with Phase Change Heat Sink"; incorporated herein by reference. In another embodiment, the heat sink includes heat conduction pipes. In another embodiment, the heat sink 120 includes phase change materials, some embodiments and material are exemplified as is described in Ser. No. 10/XXX,XXX, a co-pending patent application, entitled "Dental Light Devices Having an Improved Heat Sink", to be filed concurrently; and a U.S. Patent Application No. 60/585,224, filed Jul. 2, 2004, entitled "Dental Light Devices with Phase Change Heat Sink"; incorporated herein by reference and in U.S. Patent Application No. 60/585,224, entitled "Dental Light Devices With Phase Change Material Filled Heat Sink", filed on Jul. 2, 2004, the contents of which are incorporated herein by reference.

For example, the heat sink may include a block of thermally conductive material such as a metal having a bore or void space which is at least partially filled with a phase change material. The heat sink may include a material that more efficiently remove or divert heat from a curing light device when a reduced weight of heat sink material is used for better portability.

In one embodiment, the heat sink may include a phase change material that is more efficient in removing or diverting heat from a light source or sources with a given weight of heat sink material when compare to a heat sink made of a solid block of thermally conductive material such as metal.

In another embodiment, the heat sink may include at least one suitable phase change material including organic materials, inorganic materials and combinations thereof. These materials can undergo substantially reversible phase changes, and can typically go through a large, if not an infinite number of cycles without losing their effectiveness.

In one embodiment, the curing light 100 includes a cooling system having a compressed gas cartridge. According to one embodiment, the compressed gas cartridge is removable, and may be readily removed and replaced. During operation of the curing light 100, compressed gas is released from the cartridge. The compressed gas expands, absorbing thermal energy produced by the light source.

According to one embodiment, the compressed gas cartridge may be disposed within the housing 101, for example disposed substantially parallel to the battery pack. According to one embodiment of the invention, a single cartridge contains sufficient gas to cool the light source for a timer interval sufficient for a typical procedure. According to another embodiment of the invention, a single cartridge contains sufficient compressed gas to cool the light source for multiple procedures.

As another example, the heat sink maybe of a thermoelectric cooling type, also called "the Peltier Effect," which is a solid-state method of heat transfer through dissimilar semiconductor materials. The semiconductor materials are N and P types, with the N-type having more electrons than necessary to complete a perfect molecular lattice structure, and the P-type not having enough electrons to complete a lattice structure. The extra electrons in the N-type material and the holes left in the P-type material are called "carriers" and they are the agents that move the heat energy from the cold to the hot junction. Heat absorbed at the cold junction is pumped to the hot junction at a rate proportional to carrier current passing through the circuit and the number of couples.

The cold junction or evaporator surface becomes cold through absorption of energy by the electrons as they pass from one semiconductor to other semiconductor material or materials with dissimilar characteristics which are connected electrically in series and thermally in parallel, so that two junctions are created.

Good thermoelectric semiconductor materials such as bismuth telluride greatly impede conventional heat conduction from hot to cold areas, yet provide an easy flow for the carriers. In addition, these materials have carriers with a capacity for transferring more heat.

For a thermoelectric type heat sink, heat maybe transferred by the usual modes of conduction, convection, and radiation.

A heat sink may be constructed, for example, by hollowing out a thermally conductive material, such as metal, and at least partially filling the void with at least one phase change material prior to capping it to secure the phase change material inside, such that the at least one phase change material is substantially contained or surrounded by a thermally conductive material such as metal normally used in the construction of a conventional metal heat sink.

As another example, the heat sink may be cast or machined with thermally conductive material such as metal walls surrounding a bore or void. The bore or void is partially filed with at least one phase change material prior to capping it to secure the material inside. If desired, a heat sink may also have fins or other outer surface modifications or structures to increase surface area and enhance heat dissipation.

Other or additional features may also be included in the curing light of the present invention. For example, FIG. 12 shows a perspective view of a curing device. A switch 108*a* is provided on the top of the housing 101, while a second switch 108*b* is provided on the side of the housing 101. These switches 108*a* and 108*b* are means for turning the light emission of the light on and off and may take the form of such as a button or trigger. A timer 109 may also be provided to control the duration of time that the light is on. Other control buttons such as to set and adjust the timer (not shown) may also be present on the handle.

An audible indicator or beeper may be provided in some lights to indicate when light emission from the light module begins and ends. In one embodiment, this may be a voice alert system, verbally relating the stage and progress of the operation. In another embodiment, this may be a voice alert system, verbally relating the stage and progress of the operation as well as an auto shut off of the light source at the end of the cycle.

Figure 13:
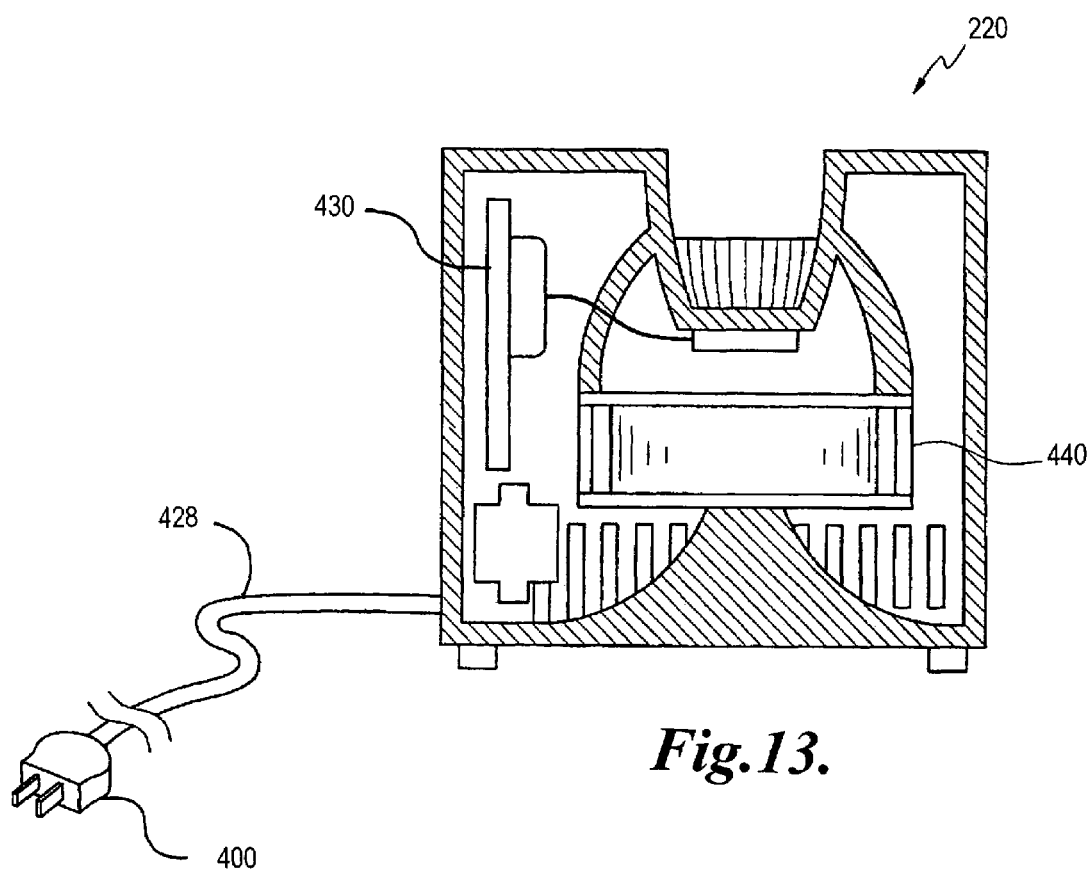
FIG. 13 shows, in cross-section, a power module for a curing light according to one embodiment of the invention.

An indicator 210 for indicating low battery power may be located on the housing 101 in a location that is easily visible to the dental professional during use concerning the status of the battery power of the battery powered curing light, as shown in FIG. 13. A second indicator 210*a* may also be located on the housing in a visible location in order to indicate to the user that the battery is being charged. These indicators may also be LEDs.

There is also a main on/off switch 230 provided at the rear or distal end 111 of the housing 101. An optional wavelength selector (not shown) may also be provided in some curing lights so that the dental professional may select the wavelength of light that he/she wishes to emit from the light, depending on the wavelength sensitivity of the photoinitiator in the light-activated material that he is using. The user may also select a combination of two or more wavelengths of light to be emitted together in some lights.

As shown in cross-section in FIG. 13, a separate battery charger module 220 is included in one embodiment. The charger module 220 is adapted to receive AC power into a plug 400 from a traditional wall socket and provide DC power to the curing light for battery charging.

The FIG. 13 battery charger module 220 has a cable 428 for conducting electricity from the plug 400 to the charger module 220. The battery charger module 220 includes circuitry 430 for controlling battery charging of batteries.

According to one embodiment, the battery charger 220 may also have a built in heat dissipation device for drawing heat away from the curing light while the battery is being charge or simply while the curing light is being rested between use cycles. In one embodiment, the heat dissipation device may include a fan 440. In another embodiment, the heat dissipation device may include a compressed air cooling system.

Figure 14:
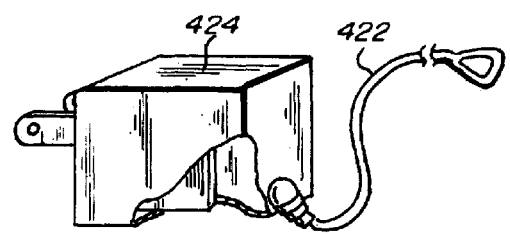
FIG. 14 shows a power module for a curing light according to another embodiment of the invention.

FIG. 14 shows a power module 420 capable of charging the battery of the curing light and (separately or simultaneously) powering the light source and control circuitry. To this end, the power module 420 includes a flexible cable 422 that is adapted to be coupled between a housing 424 of the power module 420 and the curing light.

Having described the invention by the description and illustrations above, it should be understood that these are exemplary of the invention and are not to be considered as limiting. Accordingly, the invention is not to be considered as limited by the foregoing description, but includes any equivalents.

The invention claimed is:

1. A dental curing light capable of curing light curable dental composite materials comprises a light module housing having a distal end, a proximal end, a handle and a head and neck portion, with at least one heat sink located therein, said at least one heat sink including at least two mounting platforms situated at locations of at least about 180° from each other, and at least two light sources mounted on them capable of emitting light of different wavelengths.

2. The dental curing light of claim 1 wherein the light source emitting light with a lower intensity is located closer to the proximal end of the housing.

3. The dental curing light of claim 1 wherein a larger number of light sources are mounted towards the proximal end than towards the distal end of the housing.

4. The dental curing light of claim 1 wherein at least one light source towards the distal end of the housing comprises a reflector.

5. The dental curing light of claim 2 wherein the different wavelengths have approximately the same light output intensity at the same power input when the light exits the light module housing.

6. The dental curing light of claim 1 further comprising a wavelength transformer.

7. The dental curing light of claim 6 wherein said wavelength transformer comprises at least one absorber/emitter for transforming a shorter wavelength into a longer wavelength.

8. The dental curing light of claim 7 wherein said heat sink includes a distal end having at least one mounting platform, said mounting platform comprises a well.

9. The dental curing light of claim 8 wherein said well comprises a reflecting surface.

10. The dental curing light of claim 1 wherein said heat sink comprises a phase change material.

11. The dental curing light of claim 1 further comprising a reflector for directing all light towards the proximal end of the light housing module.

12. The dental curing light of claim 11 wherein said reflector comprises multiple petals capable of varying the diameter of the output light from the curing light.

13. A dental curing light suitable for curing light curable dental composite material comprises:
 a light module housing having a distal end and a proximal end;
 at least one heat sink having a distal portion and a proximal portion, with the proximal portion located close to the proximal end of the light module housing;
 at least one mounting platform located at each portion of the heat sink; and
 at least one light source mounted on the at least one mounting platform, said light sources emitting light of different wavelengths and the light source near the proximal portion has an output intensity lower than the output intensity of the light source near the distal portion.

14. The dental curing light of claim 13 wherein said light sources are positioned in substantially opposite directions from each other.

15. The dental curing light of claim 13 wherein the light sources are located along the longitudinal axis of the housing.

16. The dental curing light of claim 13 wherein the light sources are located along an axis that is at an angle with respect to a longitudinal axis of the housing.

17. The dental curing light of claim 13 wherein said light house module comprises more than two light sources.

18. The dental curing light of claim 17 wherein said light sources are arranged in a triangle, with at least two of them closer to the proximal portion.

19. The dental curing light of claim 17 wherein more light sources are located towards the proximal portion of the heat sink.

20. The dental curing light of claim 19 wherein each of said light sources at the proximal portion has a lower output intensity than the one at the distal portion.

21. The dental curing light of claim 13 wherein said mounting platform towards the distal portion comprises a reflecting surface.

22. The dental curing light of claim 21 wherein said reflecting surface comprises a wavelength transformer.

23. A dental curing light providing light with multiple wavelengths commonly used for restorative compounds, comprises:
 a light module housing with an elongated heat sink having a well comprising at least one side wall, with a proximal end portion at the top of the well and a distal end portion at the bottom of the well; and
 at least one mounting platform located at each of the proximal end and distal end of the elongated heat sink.

24. The dental curing light of claim 23 wherein at least one light source is mounted on each of the mounting platforms on the elongated heat sink.

25. The dental curing light of claim 24 wherein all light sources are capable of emitting the same wavelength.

26. The dental curing light of claim 24 wherein the at least one light source near the distal end has an output intensity higher than the output intensity of at least one light source at the proximal end.

27. The dental curing light of claim 23 wherein said at least one mounting platforms at the distal end comprises at least one reflecting surface.

28. The dental curing light of claim 23 wherein the side wall of the well comprises a reflecting surface.

29. The dental curing light of claim 23 wherein at least two light sources are present at the proximal end of the elongated heat sink, said light sources are arranged so that the light paths overlap to produce an enhanced intensity of light output.

30. The dental curing light of claim 23 wherein each of the light sources is positioned proximate a primary heat sink mounted on the mounting platform on the elongated heat sink, the sum of the volume of the primary heat sinks being smaller than the volume of the elongate heat sink.

31. The dental curing light of claim 23 wherein at least one reflector is positioned proximate at least one light source located in the mounting platforms at the distal end of the heat sink.

32. The dental curing light of claim 31 wherein said reflector is of a parabolic shape, capable of directing the light emitted by the light source towards the proximal end of the light module housing.

33. The dental curing light of claim 23 further comprising a reflector comprising multiple sections adapted for capturing substantially all the light emitted by the light source located at the mounting platform at the distal end of the heat sink.

34. The dental curing light of claim 23 wherein said heat sink comprises a phase change material.

35. The dental curing light of claim 23 further comprising at least one wavelength transformer capable of transforming at least a portion of light emitted by a light source into a longer wavelength suitable for curing light activatable composites.

36. A dental curing light comprises:
 a light module housing having a distal end, a proximal end, a handle towards the distal end, and a head and neck portion towards the proximal end, with an elongated heat sink located in the housing towards the proximal end of the housing, said heat sink having a proximal end and a distal end;
 a light transport device at the proximal end of the housing; and
 at least one mounting platform comprising at least one light source located towards the proximal end of the elongated heat sink in substantially opposite direction to at least one mounting platform comprising at least one light source located towards the distal end of the elongated heat sink.

37. The dental curing light of claim 36 wherein the at least one light source mounted towards the distal end of the heat sink comprises at least one reflector.

38. The dental curing light of claim 36 wherein said heat sink comprises a phase change material.

39. The dental curing light of claim 36 wherein said dental curing light further comprising at one wavelength transformer capable of transforming at least a portion of light emitted by a light source suitable for curing dental composites into a longer wavelength which is also suitable for curing activatable composites.

40. The dental curing light of claim 39 wherein said at least one wavelength transformer comprises at least one absorber/emitter having at least a portion substantially transparent to the light incident on it, and at least one portion comprising a chemical capable of absorbing the incident light and emitting light having a longer wavelength.

41. The dental curing light of claim 39 wherein said at least one wavelength transformer is positioned to capture substantially all of the emitted light.

42. The dental curing light of claim 39 wherein said at least one wavelength transformer is positioned to capture at least a portion of the light emitted by the light source.

43. The dental curing light of claim 39 wherein said light transport device comprises a light guide, a focusing dome capable of varying the beam diameter of the light exiting the curing light device, a tacking tip or a combinations thereof.

44. The dental curing light of claim 43 wherein said light guide comprises at least one formation adapted for positioning the curing light to a target.

45. The dental curing light of claim 43 wherein said formation is adapted for coupling the light guide to wing-like members of a lip retracting device.

* * * * *